United States Patent [19]
Tsuchiya et al.

[11] Patent Number: 5,260,870
[45] Date of Patent: Nov. 9, 1993

[54] APPARATUS FOR MEASURING INSTANTANEOUS POWER BY LEG-STRETCHING POWER

[75] Inventors: Kunimasa Tsuchiya; Masao Ito, both of Tokyo, Japan

[73] Assignee: Combi Corporation, Tokyo, Japan

[21] Appl. No.: 615,960

[22] Filed: Nov. 20, 1990

[30] Foreign Application Priority Data

Nov. 22, 1989 [JP] Japan .................. 1-304343

[51] Int. Cl.⁵ .................. G06F 15/00; A63B 21/015
[52] U.S. Cl. .................. 364/413.02; 364/410; 482/1; 482/4; 482/5; 482/6; 482/7; 482/8; 482/79; 482/96; 482/132; 482/135; 482/110; 482/114; 482/116; 482/121
[58] Field of Search .................. 364/413.02, 410.00; 482/1, 4-8, 110, 114, 116, 121, 129, 136, 900, 901, 903, 79, 96, 132, 135; 128/25 R, 25 B; 73/379

[56] References Cited

U.S. PATENT DOCUMENTS

| | | | |
|---|---|---|---|
| 3,387,493 | 6/1968 | Strittmatter | 273/379 |
| 3,734,495 | 5/1973 | Nist et al. | 272/58 |
| 3,820,782 | 6/1974 | Salkeld | 482/135 |
| 4,550,908 | 11/1985 | Dixon | 272/130 |
| 4,621,620 | 11/1986 | Anderson | 128/25 R |
| 4,702,108 | 10/1987 | Amundsen et al. | 73/379 |
| 4,714,244 | 12/1987 | Kolomayets et al. | 272/72 |
| 4,735,410 | 4/1988 | Nobuta | 272/72 |
| 4,765,613 | 9/1988 | Voris | 272/129 |
| 4,786,051 | 11/1988 | Mullican | 272/134 |
| 5,072,929 | 12/1991 | Peterson et al. | 272/72 |
| 5,096,134 | 3/1992 | Sakano | 242/57 |

FOREIGN PATENT DOCUMENTS 0267071  9/1987  European Pat. Off.
8203228  8/1982  Netherlands.

OTHER PUBLICATIONS

"Rowing maching with break element . . . " Fichtel & Sachs AG inventor-Dumbser et al. Apr. 4, 1987.
"Computer programmable exercise apparatus . . . " by Oosthuizen AD Apr. 2, 1987.

Primary Examiner—Roy N. Envall, Jr.
Assistant Examiner—Gita D. Shingala
Attorney, Agent, or Firm—Sughrue, Mion, Zinn, Macpeak & Seas

[57] ABSTRACT

An apparatus for measuring the instantaneous power generated by a leg extension, which includes a seat provided above a drive system unit on which a subject is seated. A slide rail extends forwardly from the drive system unit, and a foot plate slides along the slide rail in forward and backward directions. A rope connected to the foot plate is provided in the drive system unit in order to be paid out in response to the forward sliding movement of the foot plate. This apparatus also includes a transmission device, which rotates in response to the rope paying-out and a powder brake, which is rotated by the transmission device. A foot load sensor is also mounted on the foot plate in order to detect the foot load developed when the subject extends his/her legs, and a rotation frequency sensor is provided at a predetermined position within the drive system unit in order to detect the rotation frequency of the powder brake. In addition, a processing unit is used to calculate the average speed, the average muscle power, the average power and the peak power generated by the subject's legs, according to the detection signals from the foot load sensor and the rotation frequency sensor. These calculations are visually and auditorily displayed to the subject by an indicator device.

9 Claims, 5 Drawing Sheets

APPARATUS FOR MEASURING INSTANTANEOUS POWER BY LEG-STRETCHING POWER

BACKGROUND OF THE INVENTION

This invention relates to an apparatus used for measuring the physical strength of a person. More specifically, the invention relates to an apparatus which dynamically measures the instantaneous power output of a single leg muscle, via the leg extending power of the subject. The present invention also monitors forms of motion by measuring the instantaneous power of a multi-articular motion such as a vertical jump.

The following problems have been noted with respect to conventional physical strength tests such as a vertical jump test, a reciprocal jump test and a dorsal muscle test.

(1) It is difficult to link the test results with a synthetic appraisal, since various functions are appraised separately.

(2) Appraisal standards are ambiguous. For example, with respect to a vertical jump, the appraisal standard is the height to which one can jump; however, this is an index of the performance, and is an indirect and substitutive appraisal of the physical strength.

(3) There is no standardized scientific proof, which relates an index of performance (i.e. a persons vertical jump) to physical strength.

(4) Often the test subject must perform unusual movements with a large load, which often result in injury. Recently, an increased interest in physical strength has generated a demand for a method and apparatus, which measures physical strength easily, safely and accurately. Also, a study has been made, which creates an index of the physical strength based on the power theory.

In the power theory, physical strength is measured as the capacity of the energy (integrating value of the power), or the power is measured as an index. Forms of power development are classified according to energy developing mechanisms (i.e. specific muscles) in a living body. Within each form of development, the upper limit value of power is measured while monitoring the corresponding energy developing mechanism (muscle). This measured upper limit is used as an index of physical strength in the corresponding energy developing mechanism.

Specifically, the measurements are carried out in the following manner:

(a) Oxygen-present energy mechanism
Duration: Infinite
Appraisal of upper limit power: Power available at 75% of the maximum heat rate, etc.
Main factor for energy generation: Oxygen (b) Lactic acid-type anoxia energy mechanism
Duration: About 30 seconds
Appraisal of upper limit power: Average power, critical power, etc.
Main factor for energy generation: Glycogen (c) Non-lactic acid-type anoxia energy mechanism
Duration: About 7 seconds
Appraisal of upper limit power: The optimum value determined by speed and developing force of the peak power around approximately 5 to 6 seconds.
Main factor for energy generation: ATP-CP type chemical energy.

In connection with the above energy mechanisms (a) and (c), a measurement apparatus utilizing a bicycle ergometer has been proposed by the Applicant of the present invention (Japanese Patent Publication No. 42694/89), and there are known "AEROBIKE" and "POWERMAX" (both of which are registered and pending trademarks of Konbi Corporation; the former is Japanese Trademark Registration No. 1840771, and the latter is Japanese Trademark Publication No. 42348/86) to which the above techniques are applied.

The energy mechanism of example (b) can be carried out with a Wingate test. An apparatus for measuring an instantaneous power of the subject utilizes a bicycle ergometer, since the pedaling motion is analogous to a usual running motion and is rhythmic. The power can be produced efficiently, with less injuries resulting.

On the other hand, with respect to a continuous leg muscle power exercise or other similar multi-articular exercise, the instantaneous power of a single leg muscle is also an important factor, for example, when hastily avoiding an obstacle in daily life. An apparatus is known, which measures the instantaneous power of a single developing leg muscle, for example, as disclosed in Japanese Laid-Open (Kokai) Utility Model Application No. 18103/88. In this application, a leg's extension power is received by a hydraulic or pneumatic cylinder, and the physical strength of the subject is measured according to data from the cylinder.

However, in the above leg extension measuring apparatus, the adjustment of the cylinder is very difficult. In addition, since the load varies in accordance with the speed, it is difficult to accurately measure the instantaneous power.

Further, when using the hydraulic cylinder, the response time of the hydraulic pressure is slow, which prevents an accurate measurement.

SUMMARY OF THE INVENTION

The present invention, which has been made to solve the foregoing problems, is directed to the accurate measurement (based upon a power theory) of an instantaneous power, while eliminating unstable factors of the measuring system as much as possible.

It is an object of this invention to provide an apparatus for measuring the instantaneous power of a leg extension muscle, in which a powder brake is used in order to reduce the influence of the inertia on the power measurement. In addition, as compared with the conventional power measurement based on the non-lactic acid-type anoxia energy mechanism, the present invention shortens the time required to push a foot plate, thereby reducing the burden of the measurement on the subject.

Another object is to provide an apparatus for measuring an instantaneous power of a leg extending muscle, in which the device used to produce the load is not hydraulic or of a dynamo type but a powder break having a characteristic to which a torque of the powder break does not depend upon the rotation frequency thereof, since the magnitude of the load produced by these devices varies with the foot-pressing speed. Instead, the present invention produces a load with a constant torque to which an amount of the constant torque is regarded as a weight of a subject corresponding to a break force of foot plate in consideration of the subject maintaining the weight thereof by legs of the subject, independent of the foot-pressing speed, thereby stabilizing the measurement.

A further object is to provide an apparatus for measuring an instantaneous power of a leg extending muscle, in which the angle of the foot plate is automatically varied in accordance with the amount of leg extension. Previously, the angle of the foot plate was fixed, which caused the foot-pressing force to be unstable because of a change in the angle of inclination of the foot sole during the leg extension.

Within the present invention, the powder brake is used as the constant-torque low-inertia load mechanism, and the instantaneous power is measured by kicking the foot plate with the subject's full power for a very short time. Therefore, because of the kicking which is a natural form of exercise, the physical burden on the subject is lessened, the measurement of the leg extension of the subject is easier, and the accuracy of the instantaneous power measurement is higher. With respect to forms of motion, because of the above full power kicking, the instantaneous power of the dynamic single-developing multi-articular motion, such as a vertical jump, can be measured.

DETAILED DESCRIPTION OF THE PRESENT INVENTION

Figure 1:
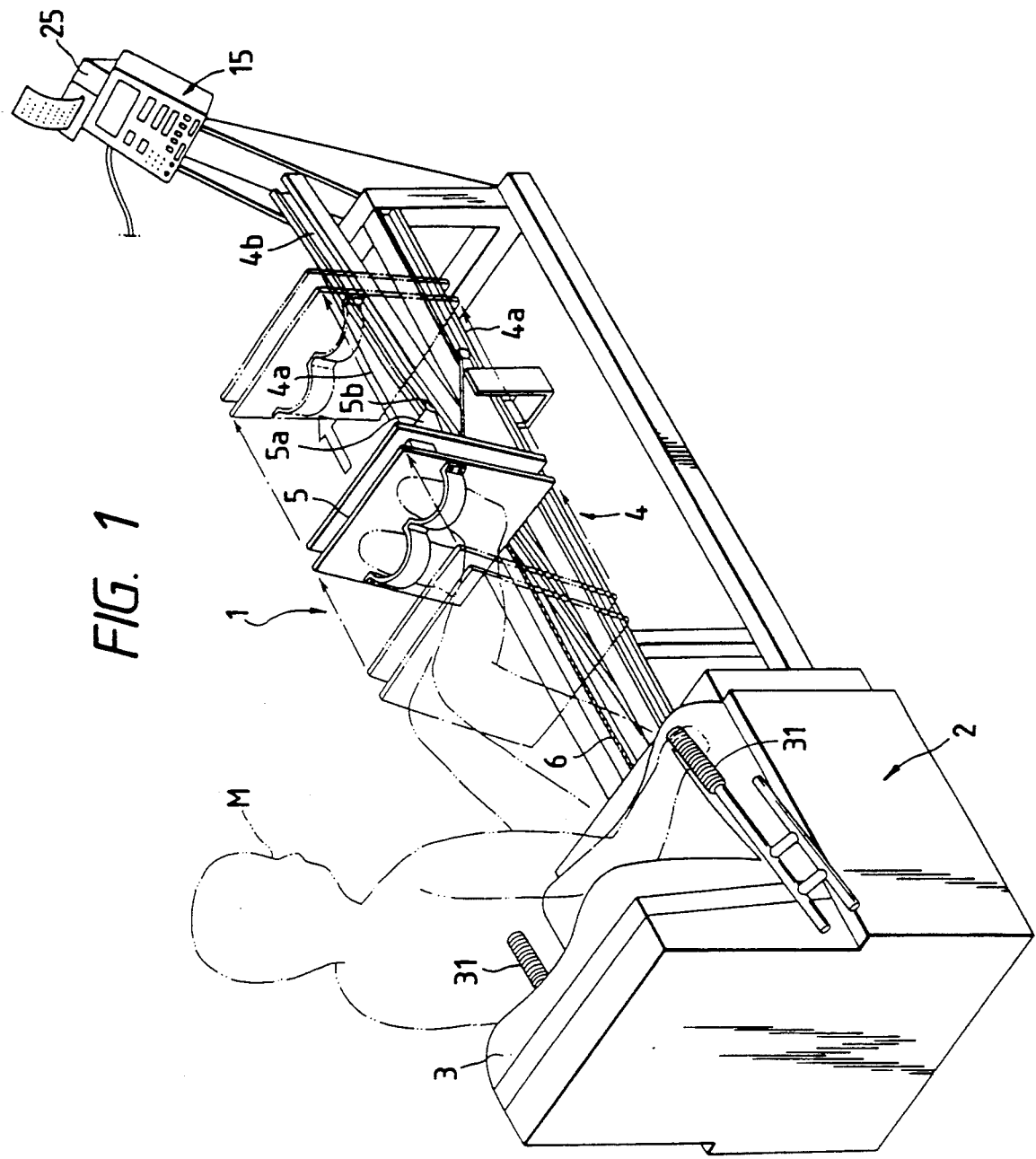
FIG. 1 is a perspective view of the overall construction of an apparatus for measuring the instantaneous power of a leg extension muscle, provided in accordance with the present invention.

One example of an apparatus for measuring the instantaneous power of a leg extension, constituting a preferred embodiment of the present invention, will now be described with reference to the drawings.

In the drawings, the overall construction of the apparatus for measuring an instantaneous power of a leg extension is designated by reference numeral 1. The apparatus 1 comprises a seat 3 provided above a drive system unit 2 on which the subject M is to be seated. A slide rail 4 extends forwardly from the drive system unit 2 and a foot plate 5 slides along the slide rail 4 in forward and backward directions. The angle of inclination of the foot plate 5 is variable in accordance with a variation of the angle of the foot sole of the subject M caused by the extension of the subject's legs. A drum 7 mounted within the drive system unit 2 has a rope 6 wound therearound, which is paid out in response to the forward sliding movement of the foot plate 5. A return spring 8 is mounted on the side of the drum 7 in order to rewind the paid-out rope 6 on the drum 7. The return spring 8 is in the form of a cylindrical spring as shown in the drawings. A transmission device 9 is used to rotate of the drum 7 and the powder brake 10 in one direction. A foot load sensor 11 is mounted on the foot plate 5 in order to detect the foot load developed (force) when the subject M extends his/her legs.

Figure 2:
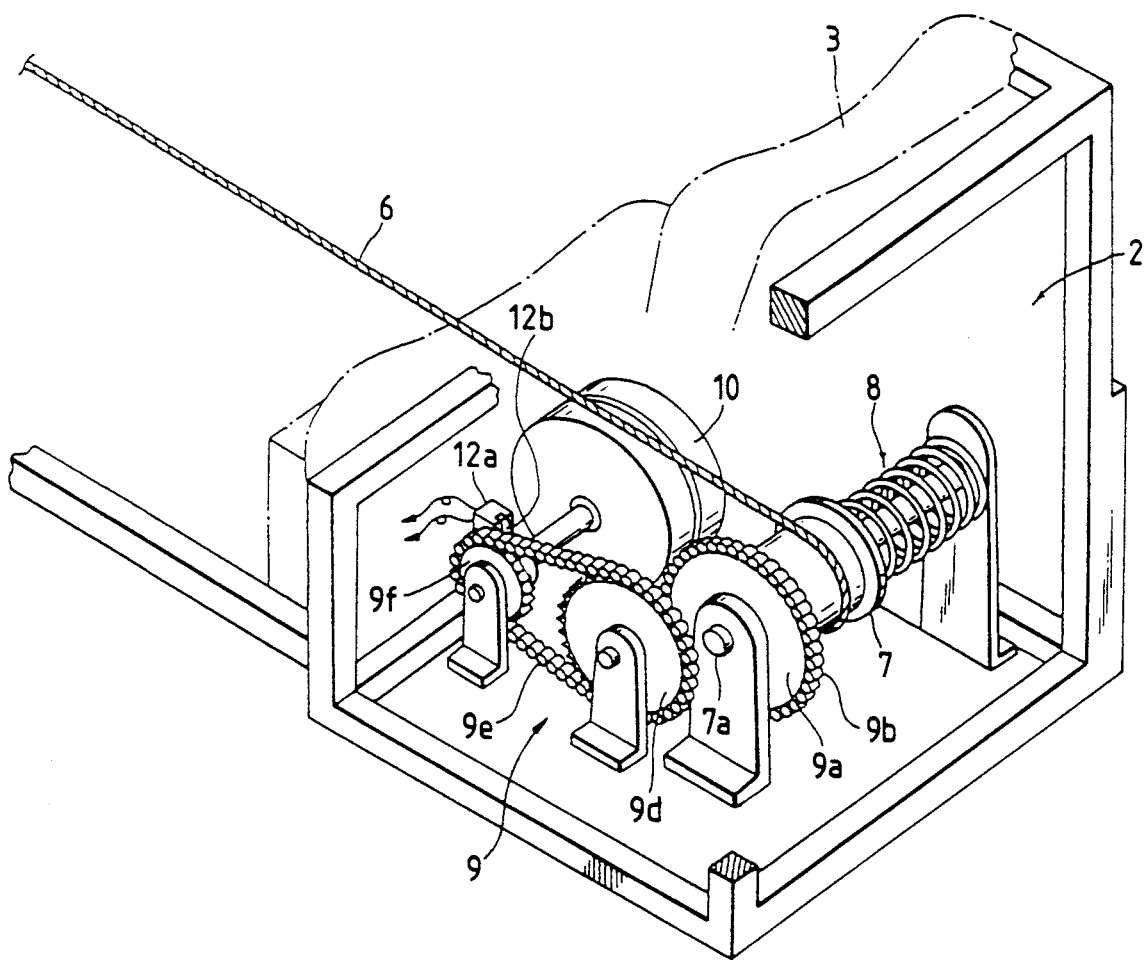
FIGS. 2 and 3 are perspective views of important portions within a drive unit, respectively.
Figure 5:
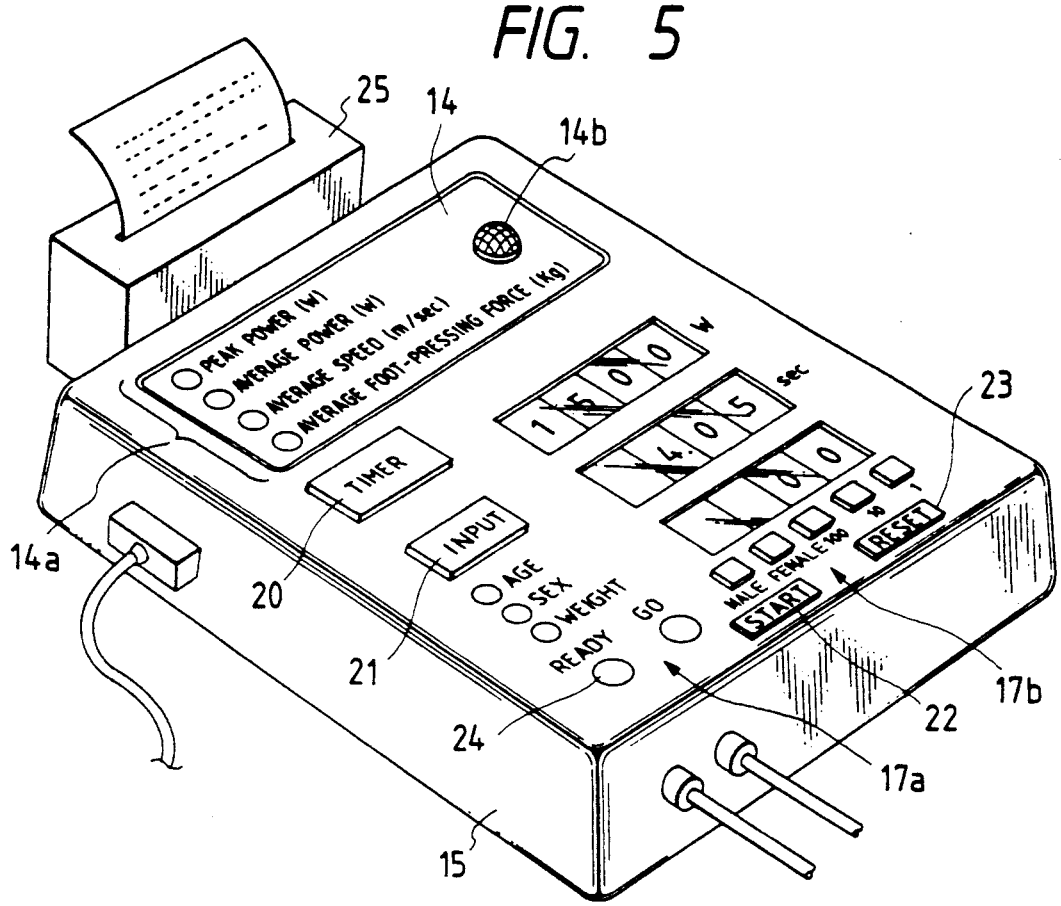
FIG. 5 is a perspective view of a control panel.
Figure 6:
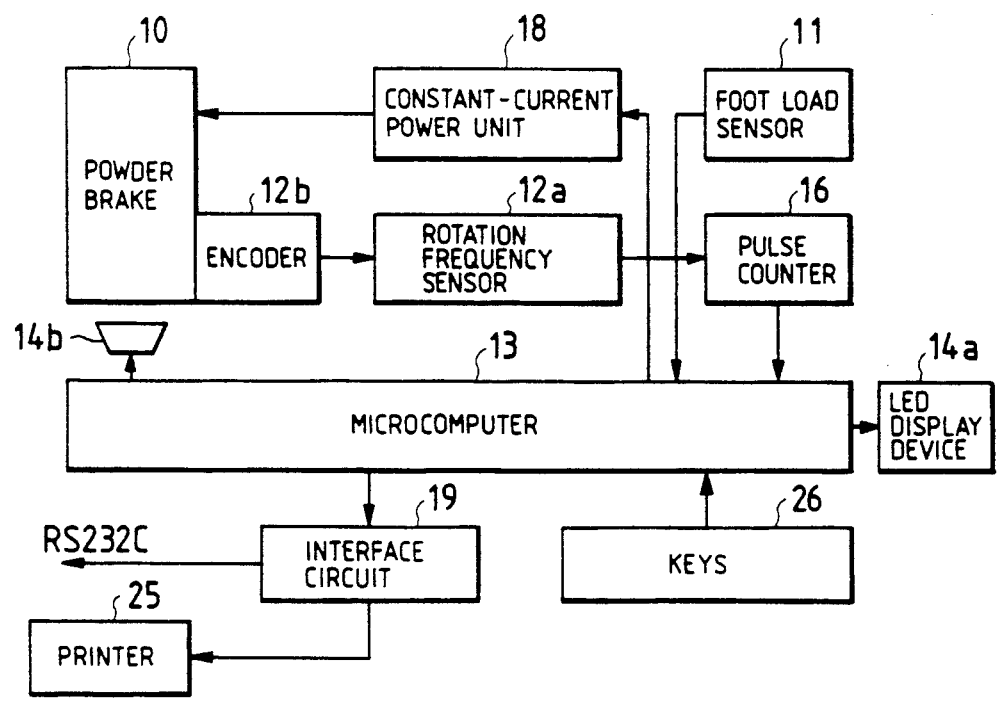
FIG. 6 is a block diagram of a control portion including a processing unit.

The present invention also includes a rotation frequency sensor 12, provided on the side of the powder brake 10 as shown in FIG. 2, to detect the rotation frequency of the powder brake 10. The rotation frequency sensor 12 and foot load sensor 11 are connected to a processing unit 13, which calculates (based upon the power theory) the average speed (m/sec), the average foot-pressing force (kg), the average power (W) and the peak power (W) at the time the subject M extends his/her legs. An indicator device 14 visually and auditorially indicates data processed by the processing unit 13 (hereinafter referred to as "microcomputer"). This indicator device 14 comprises a LED display device 14a, a buzzer 14b and etc., as shown in FIGS. 5 and 6.

Since the powder brake 10 has a constant-torque and low-inertia load function, it is capable of providing accurate data, which is proportional to the physical strength (i.e., foot pressing force) of the subject. For this reason, the powder brake of the present invention is used as the load device.

The slide rail 4 comprises right and left horizontal slide rails 4a and 4a (FIG. 1), and an inclined slide rail 4b disposed centrally and slanted upwardly in a forward direction. A guide roller 5b mounted on a lower end of a bracket 5a mounted on the reverse face of the foot plate 5 is received in the inclined slide rail 4b, so that the upstanding angle of the foot plate 5 slidable along the slide rail 4 in forward and backward directions can be varied. Handles 31 are also provided for the subject M to grasp for stabilizing his sitting posture.

Figure 3:
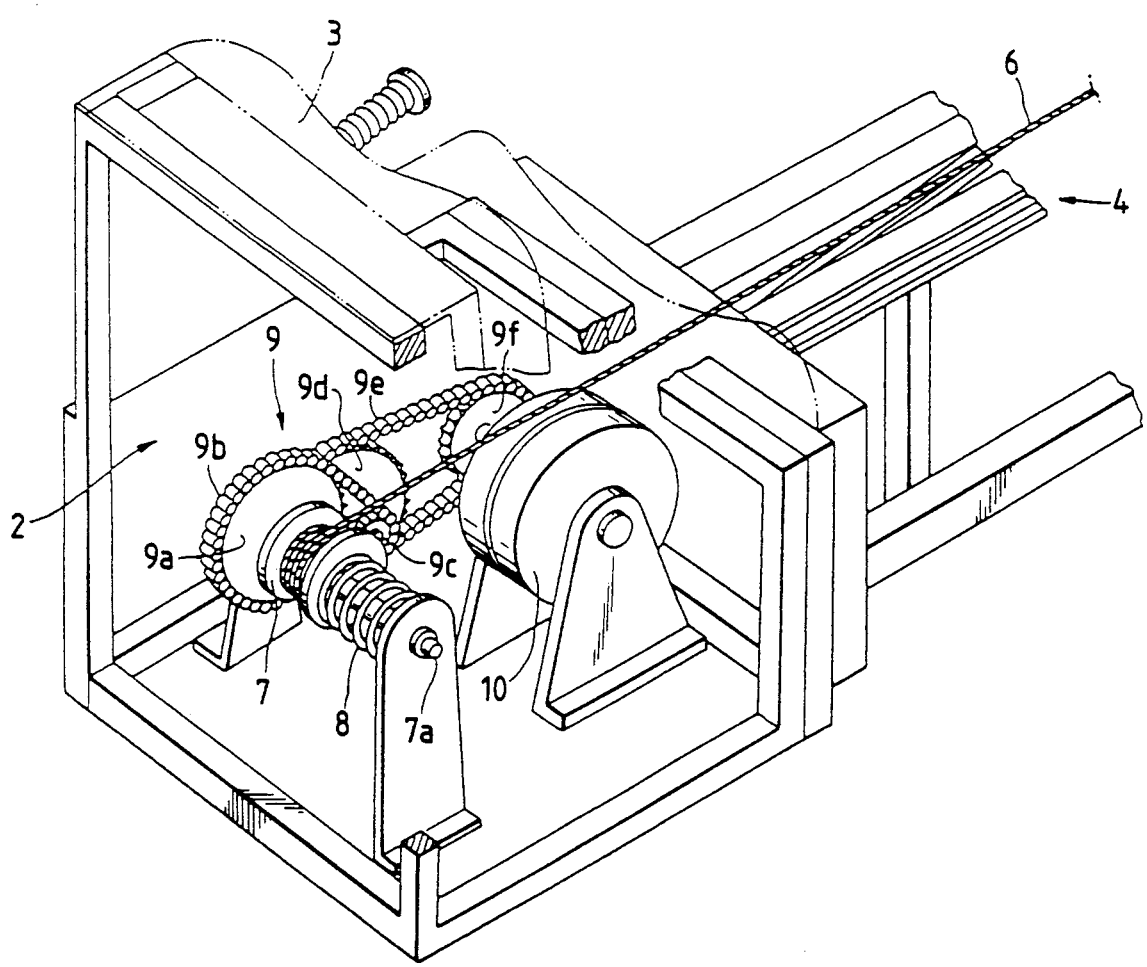
Figure 4:
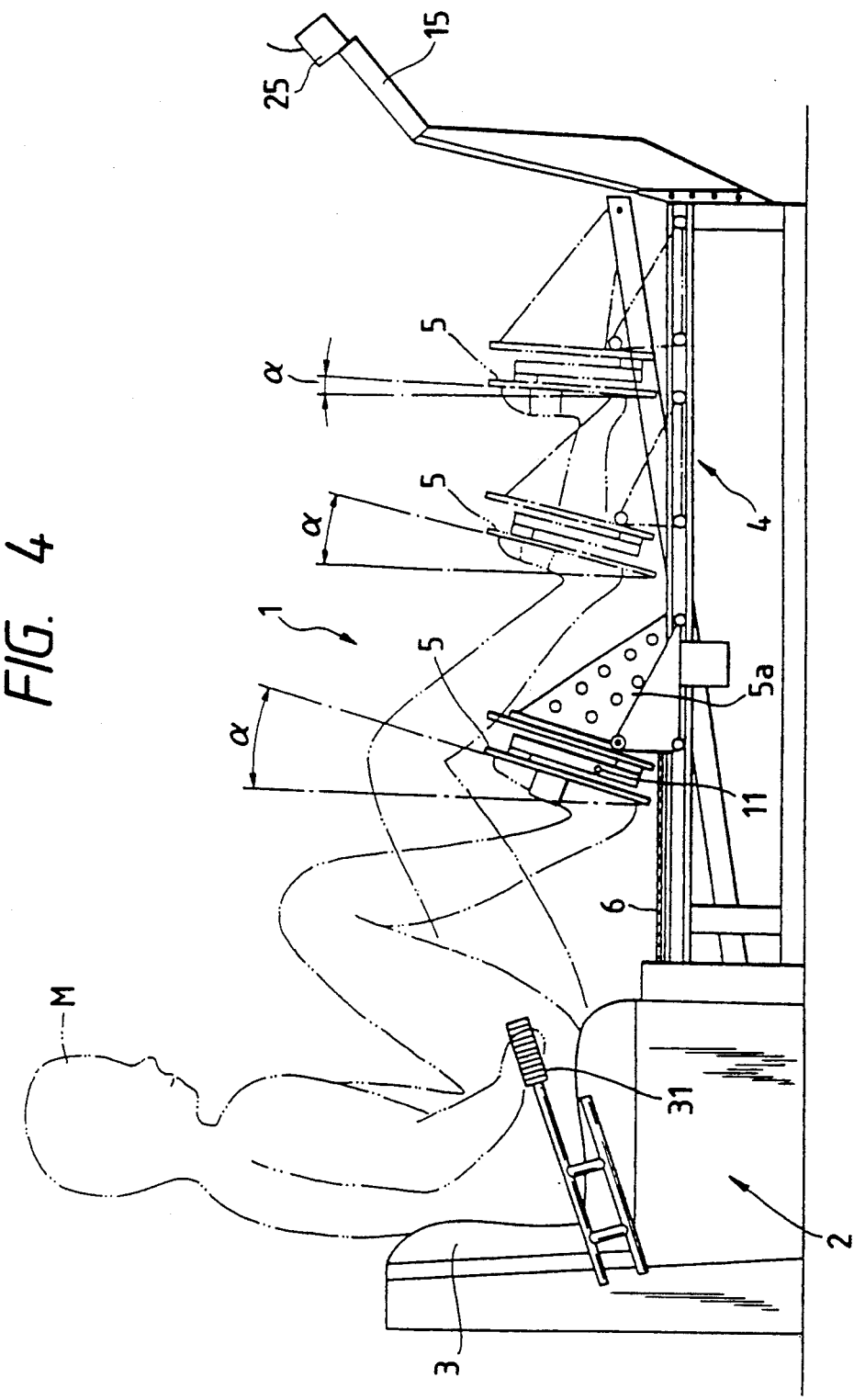
FIG. 4 is a side-elevational view of the overall construction.

As shown in FIGS. 2 and 3, the transmitting device 9, which transmits the rotation of the drum 7 to the powder brake 10, 7 comprises a sprocket 9a mounted on a rotation shaft 7a of the drum 7 and a free wheel 9c rotated in one direction by a chain 9b extending around the sprocket 9a. Transmitting device 9 also includes a sprocket 9d mounted on a rotation shaft of free wheel 9c, and a sprocket 9f rotated by a chain 9e extended around the sprocket 9d. The rotation shaft of the sprocket 9f also serves as an output shaft of the powder brake 10.

As shown in FIGS. 1 and 5, the LED display device 14a and the buzzer 14b, which visually and auditorially indicate the average speed (m/sec), the average foot-pressing force (kg), the average power (W) and the peak power (W), are mounted on a control panel 15 mounted on the front end of the slide rail 4. Rotation frequency pulse from an encoder 12b disposed on an axis of the powder brake 10 are fed via the rotation frequency sensor 12a to a pulse counter 16 (FIG. 6), which counts the input pulses at sampling intervals and feeds the microcomputer 13 digital data corresponding to the speed with which the foot plate 5 moves.

As shown in FIGS. 5 and 6, data from switches 17a and 17b, are also transmitted to the microcomputer 13, from which predetermined processing is carried out based on the power theory, so that the average speed (m/sec) such as a horizontal component of an instant speed of the foot plate 5 when the subject brings his legs into an extended position is averaged by the time of period from a bent position to the extended position in his legs, the average foot-pressing force (kg) such as an instant foot pressing force of an output of the load sensor 11 is averaged in the same manner described above, the average power (W) which is averaged in the same manner described above, the peak power (W), etc., are displayed on the indicator device 14. Also, the microcomputer 13 feeds a predetermined current to the powder brake 10 via a constant voltage power unit 18 in accordance with a curve for current-torque having a load characteristic which has been measured in order to apply a force of a predetermined weight decided by key operation to the foot plate 5. The various data of the microcomputer 13 are supplied to a host computer (not shown) via an interface circuit 19, which manages the measurement results.

In FIG. 5, reference numeral 20 denotes a timer indicator, reference numeral 21 an input switch, reference numeral 22 a start switch, reference numeral 23 a reset switch, reference numeral 24 a ready switch, reference numeral 25 a printer, and reference numeral 26 a ten-key. The various data of the subject M are inputted by these switches so that desired parameters can be set.

The manner of use and the operation of the above apparatus for measuring an instantaneous power of a leg extension operation, provided in accordance with the present invention, will now be described in detail.

(1) First, in view of his physical strength, his exercise experience and etc., the subject M, before sitting on the seat 3, inputs parameters (i.e., his weight and so on) necessary for the measurement through the switches on the control panel 15.

(2) Then, the subject M properly sits on the seat 3, and moves the foot plate 5, extending upwardly above the slide rail 4, toward him. The subject M bends his legs and places his feet on the foot plate 5, with his hands firmly grasping the right and left handles 31. When the buzzer 14b produces sound, the subject vigorously kicks with his legs in a forward direction so as to push the foot plate 5 toward the front side of the slide rail 4. As a result of the kicking of the foot plate 5, the rope 6 connected to the foot plate 5 is vigorously paid out, so that the drum 7 is rotated against the bias of the return spring 8. The rotation of the drum 7 is transmitted to the powder brake 10 via the transmission device 9, that is, via the sprocket 9a, the chain 9b, the free wheel 9c, the sprocket 9d, the chain 9e and the sprocket 9f.

(3) By the above procedure, the first kicking of the foot plate 5 is completed.

(4) Next, when the subject M brings his extended legs into the initial bent position, the paid out rope 6 is rewound on the drum 7 under the bias of the return spring 8, so that the foot plate 5 is automatically returned to the original position, thereby preventing undesired loosening of the rope 6.

(5) Subsequently, the above kicking motion is repeated a predetermined number of times within a predetermined time period.

(6) The foot-pressing load applied by the extended legs during the above kicking motion is accurately detected by the foot load sensor 11. Also, the rotation of the powder brake 10 is accurately detected by the rotation frequency sensor 12. These detection signals are inputted into the microcomputer 13, and based on the power theory, the microcomputer 13 measures the average speed (m/sec), the average foot-pressing force (kg), the average power (W) and the peak power (W) at the time of the subject M extends his/her legs. This data is displayed on the LED display device 14a provided on the control panel 15, and outputted from the printer 25.

(7) The above kicking exercise is terminated when the buzzer 14b indicates that the predetermined time period is over.

As described in detail above, the powder brake is used as the constant-torque low-inertia load mechanism, and the instantaneous power is measured through the kicking of the foot plate with the subject's full power for a very short time.

Therefore, because of the kicking which is a natural form of exercise, a physical burden on the subject is less, the leg measurement is easy, and the measurement accuracy is high. With respect to forms of motion, because of the above full power kicking, the instantaneous power of the dynamic single-developing multi-articular motion such as a vertical jump can be measured, and other various advantages are achieved.

What is claimed is:

1. An apparatus for measuring an instantaneous power generated during a leg extending motion, said apparatus comprising:
   a seat provided above a drive system unit on which a subject is seated;
   a slide rail extending forwardly from the drive system unit;
   a foot plate slidably connected to the slide rail, wherein said foot plate slides in a forward direction in response to a leg extension motion of said subject;
   a rope provided in the drive system unit, said rope being connected to said foot plate and being paid out of said drive system unit in response to the forward sliding movement of the foot plate;
   a transmission device rotated by said rope, as said rope is paid out of said control device;
   a powder brake rotated by the transmission device;
   foot load sensor means, mounted on the foot plate, for detecting a foot load developed during operation of the apparatus;
   rotation frequency sensor means, provided within the drive system unit, for detecting a rotation frequency of the powder brake;
   processing means for calculating an average speed, an average muscle power, an average power and a peak power generated during a leg extension operation performed by said subject, wherein said processing means performs said calculations in accordance with detection signals from said foot load sensor means and said rotation frequency sensor means; and
   indicator means for visually and auditorially indicating processing data calculated by said processing means.

2. The apparatus of claim 1, said rope being wound upon a drum such that said drum rotates while said rope is paid out in response to the sliding movement of the foot plate, the rotation of said drum being transmitted to the transmission device.

3. The apparatus of claim 2, wherein the rope is rewound upon said drum by a return spring.

4. The apparatus of any one of claims 1 to 3, wherein an angle of inclination of the foot plate is variable in accordance with variation of an angle of a foot sole of the subject, which is caused in response to the sliding movement of the foot plate.

5. The apparatus of claim 4, wherein said slide rail is upwardly inclined in a forward direction such that said slide rail causes said variation in the angle of inclination of said foot plate as the foot plate slides along the slide rail.

6. The apparatus of claim 1, wherein said powder brake provides a constant-torque and low-inertia load resistance against said foot plate, such that said powder brake reduces the inertial influence upon the calculations performed by said processing means.

7. The apparatus of claim 6, wherein said processing means transmits a control signal to said powder brake in order to control the load resistance produced by said powder brake.

8. An apparatus for measuring an instantaneous power generated during a leg motion, said apparatus comprising:
  a seat for supporting an exerciser;
  a movably disposed foot member for receiving at least one of the feet of the exerciser, said foot member being moved in a forward direction in response to a leg motion of said exerciser;
  a load means for exerting a load on said foot member so as to resist movement of said foot member in said forward direction;
  foot load sensor means, mounted on the foot member, for detecting a foot load developed during said leg motion;
  rotation frequency sensor means, provided within said load means, for detecting a rotation frequency of said load means;
  processing means for calculating at least one of an average speed, an average muscle power, an average power and a peak power generated during said leg motion performed by said exerciser, wherein said processing means performs said calculation in accordance with detection signals from said foot load sensor means and said rotation frequency sensor means; and
  indicator means for visually and auditorially indicating processing data calculated by said processing means.

9. The apparatus of claim 8, wherein said processing means calculates each of said average speed, average muscle power, average power and peak power.

* * * * *